United States Patent [19]

Schnur et al.

[11] Patent Number: 5,344,967
[45] Date of Patent: Sep. 6, 1994

[54] TREATMENT OF ORGANIC SULFONIC ACID

[75] Inventors: Eric R. Schnur, Mentor; David L. Westfall, North Olmsted, both of Ohio

[73] Assignee: The Lubrizol Corporation, Wickliffe, Ohio

[21] Appl. No.: 723,144

[22] Filed: Jun. 28, 1991

[51] Int. Cl.$^5$ ............................................. C07C 193/24
[52] U.S. Cl. ........................................ 562/94; 562/45; 562/93; 562/91
[58] Field of Search ................. 562/45, 92, 96, 96, 562/94, 93

[56] References Cited

U.S. PATENT DOCUMENTS 4,153,627  5/1979  Delbende et al. .................... 562/92

FOREIGN PATENT DOCUMENTS 0002907  7/1979  European Pat. Off. ............. 562/45
2341565  9/1977  France ................................. 562/45

OTHER PUBLICATIONS

Kohl and Resenfeld, Chem. Eng. 66(12) 127 (1959), pp. 14–2.

Primary Examiner—Jose' G. Dees
Assistant Examiner—Keith MacMillan
Attorney, Agent, or Firm—Forrest L. Collins; Frederick D. Hunter

[57] ABSTRACT

The present invention describes treating an organic sulfonic acid with an olefin to obtain an improvement in color of the resultant salts and to lessen the amount of inactive components in the composition.

35 Claims, No Drawings

TREATMENT OF ORGANIC SULFONIC ACID

BACKGROUND OF THE INVENTION

The present invention relates to the treatment of organic sulfonic acids through the use of a high molecular weight unsaturated hydrocarbons, or mixtures of unsaturated hydrocarbons and includes as an optional step heat treatment.

INTRODUCTION TO THE INVENTION

Alkyl benzene sulfonates are highly useful materials for the preparation of detergents for lubricating oils. Alkyl benzene sulfonates are also utilized for laundry detergent compositions. It is noted in the processing of sulfonic acids that some discoloration may occur particularly upon heating. A second effect on organic sulfonic acids is the development of a darkening of the product which may be related to the sulfonating agent. The present invention also deals with methods of reducing the amount of inactive components as later described herein from a mixture of organic sulfonic acids.

U.S. Pat. No. 4,153,627 issued May 8, 1979 to Delbende et al discusses the treatment of sulfonic acids and sulfonates containing olefins and water to improve the color and thermal stability of the composition. Tirtiaux in U.S. Pat. No. 4,259,193 issued Mar. 31, 1981 teaches obtaining overbased alkaline earth metals sulfonates from monoalkyl orthoxylene or toluene. The overbased sulfonates of Tirtiaux et al are stated to be useful as detergents for lubricating oils.

A process for treating a dimer obtained from a boron trifluoride oligomerization process is conducted by reacting the same with an alpha-olefin in the presence of a phosphoric acid-modified boron trifluoride catalyst as reported by Blewett et al in U.S. Pat. No. 4,469,912 issued Sep. 4, 1984 Benson et al in U.S. Pat. No. 3,681,443 issued Aug. 1, 1972 teaches the retardation of formation of color-forming bodies in alkyl aryl sulfonic acids through the use of small amounts of beta-unsaturated carboxylic acids such as maleic anhydride.

Prillieux in U.S. Pat. No. 4,618,458 issued Oct. 21, 1986 teaches the purification of sulfuric acid rich sulfonic acids, in particular those prepared by oleum sulfonation, through water washing, and treatment with an olefin and final heat treatment.

The production of olefins is taught in U.S. Pat. No. 2,387,784 issued Oct. 30, 1945 to Thomas et al. A further teaching in the production of olefins is found in U.S. Pat. No. 2,404,788 issued to Burk et al on Jul. 30, 1946. The alkylation of various organic compounds including aromatic materials is taught by Axe in U.S. Pat. No. 2,404,897 issued Jul. 30, 1946.

The preparation of ethylene polymers is found in U.S. Pat. 2,962,489 issued Nov. 29, 1960 to Zeldin. Thomas in U.S. Pat. No. 2,976,338 issued Mar. 21, 1961 teaches the use of polyphosphoric acid-boron trifluoride catalyst to polymerize olefins.

Further teachings on the polymerization of liquid olefins using boron fluoride-phosphoric acid catalyst systems are found in U.S. Pat. No. 2,816,944 issued Dec. 17, 1957 to Muessig et al. The polymerization of propylene, particularly in the 300 to 800 molecular weight range, is taught in U.S. Pat. No. 2,960,552 issued Nov. 15, 1960 to Wasley.

The present invention improves upon and renders more cost effective the production of sulfonate products of aromatic compounds substituted with a hydrocarbyl group.

Throughout the specification and claims percentages and ratios are given by weight, temperatures are in degrees Celsius, and pressures are in KPa gauge unless otherwise indicated. To the extent that the foregoing references are applicable to the present invention they are herein incorporated by reference.

SUMMARY OF THE INVENTION

The present invention describes a process of treating an organic sulfonic acid, the steps comprising contacting the organic sulfonic acid with at least 0.3 weight part of an unsaturated hydrocarbon per 100 weight parts of the organic sulfonic acid to obtain a mixture, wherein the unsaturated hydrocarbon has a number average molecular weight between about 600 and 3,000.

The present invention further describes a process of treating a mixture of an alkyl substituted aromatic sulfonic acid and a source of sulfur dioxide wherein an alkyl substituted aromatic compound is contacted with a sulfonating agent to obtain the alkyl substituted aromatic sulfonic acid, and the alkyl substituted aromatic sulfonic acid and source of sulfur dioxide is then processed to reduce the sulfur dioxide content of the mixture by introducing a relatively non-reactive gas to the mixture and maintaining the mixture at a temperature of about 70° F. (23° C.) to about 175° F. (80° C.) for a period of time sufficient to reduce the sulfur dioxide content, and contacting the resultant alkyl substituted aromatic sulfonic acid with an unsaturated hydrocarbon having a number average molecular weight between about 600 and 3,000.

As a further aspect of the present invention there is described a composition of matter comprising an organic sulfonic acid and unsaturated hydrocarbon having a number average molecular weight between about 600 and 3,000.

The invention herein also describes a composition of matter which is an organic sulfonate obtained by the process of contacting an organic sulfonic acid with at least 0.3 weight part of an unsaturated hydrocarbon wherein the unsaturated hydrocarbon has a number average molecular weight between about 600 and 3,000 per 100 weight parts of the organic sulfonic acid, and converting the organic sulfonic acid to the organic sulfonate.

Yet a further embodiment of the present invention is a composition of matter comprising an alkyl substituted aromatic sulfonate and an unsaturated hydrocarbon having a number average molecular weight of about 600 to about 3,000 obtained by the process of forming a mixture of an alkyl substituted aromatic sulfonic acid and a source of sulfur dioxide wherein an alkyl substituted aromatic compound is contacted with a sulfonating agent to obtain the alkyl substituted aromatic sulfonic acid, and the alkyl substituted aromatic sulfonic acid and the source of sulfur dioxide is processed to reduce the sulfur dioxide content by introducing a nonreactive gas to the mixture at a temperature of about 70° F. (23° C.) to about 175° F. (80° C.) for a period of time sufficient to reduce the sulfur dioxide content, contacting the alkyl substituted aromatic sulfonic acid with the unsaturated hydrocarbon, and converting the alkyl substituted aromatic sulfonic acid to a salt thereby obtaining the alkyl substituted aromatic sulfonate.

DETAILED DESCRIPTION OF THE INVENTION

The present invention as previously discussed is dependant on the treatment of an organic sulfonic acid. The organic sulfonic acid may be any material which is useful for the synthesis of a detergent, and in particular as a detergent for a motor vehicle oil.

The preferred organic sulfonic acids are those obtained through the alkylation of benzene, toluene or xylene. The foregoing aromatic compounds typically reacted with an alkylating agent which contains a $>C=C<$ group The alkylating agents are frequently obtained from lower alkene monomers which have been polymerized to give a lower alkene polymer having a molecular weight of about 250, preferably about 300 to about 500. The preferred lower alkene monomers for obtaining the alkylating agent are obtained as follows.

The polymerization of the lower alkene monomer to the polymer desirably gives a product which contains a high vinylidene content. A vinylidene structure is as follows:

$$(R)_2C=CH_2 \qquad (A)$$

where each R group contains at least one carbon atom. As the various R groups become more complex, the later described alkylation process becomes more difficult. Moreover, the presence of a significant amount of trisubstituted olefin (B) or tetrasubstituted olefin (C), as shown below, significantly reduces the reactivity in alkylation reactions.

$$(R)_2C=CH(R) \qquad (B)$$

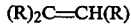

$$(R)_2C=C(R)_2 \qquad (C)$$

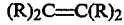

Thus, internal olefins are not as reactive in alkylation reactions as are vinylidene components.

In the present invention, the vinylidene content may be augmented by any alpha-olefin content present in the product or added to the product. An alpha-olefin is of the formula:

$$RHC=CH_2 \qquad (D)$$

where R is as previously described.

For convenience in defining the present invention, the following criteria is employed. The vinylidene content of the total mono-unsaturation present is typically at least about 15%, more typically 20% and most typically at least 25%. The weight ratio of vinylidene to trisubstituted olefin is about 1:4 to about 8:1, typically about 1:3 to about 5:1, and often at least 1:4 and more typically at least 1:3. The amount of vinylidene and other substituted olefins are conveniently obtained by carbon 13 NMR as referred to in Determination of *Molecular Structure of Hydrocarbon Olefins by High Resolution Nuclear Magnetic Resonance,* Stehling et al, *Anal Chem.,* 38, (11), pp 1467-1478 (1966). See also $^{13}C$ *Chemical Shifts of Some Model Olefins* by Couperus et al, *Org. Magn. Reson.* 8, pp. 426-431 (1976). The foregoing articles are incorporated by reference.

In conjunction with the vinylidene content, it is preferred that the unsaturation content of the polymer is as defined as above and determined by ASTM D-1159-66 (Reapproved 1970) herein incorporated by reference.

The lower alkene polymer is obtained from a lower alkene monomer typically containing from about 2 to about 6 carbon atoms. Typically, the lower alkene monomer contains from about 2 to 4 carbon atoms such as butene and most preferably propylene(propene).

The feed stream of the lower alkene monomer is preferably free of diene or higher moieties. The diene or higher unsaturated moieties can lead to the formation of diphenyl alkanes upon alkylation. By being substantially free of diene moieties, it is desired that there be no more than 10%, preferably no more than 5% by weight of diene or higher unsaturated moieties present in the feed stream. Most preferably, it is desired that the feed stream be completely free of diene moieties.

It is also highly desired that the alkene monomer is an alpha olefin such as the propylene or butene. By alpha olefin is meant that the unsaturation in the alkene monomer is between the first and second carbon atoms in the molecular structure. A further desired feature of the present invention is where the lower alkene monomer is at least 95% of a single species. By single species, it is meant that a single lower alkene monomer is the predominant species within the feed stream. That is, where the lower alkene monomer contains 4 carbon atoms, it is desirable that the monomer is substantially pure 1-butene rather than in a mixture with 2-butene or isobutylene. Of course, for the preferred propene only one isomer, e.g., 1-propene, exists.

The feed streams for the present invention are typically obtained through catalytic cracking of petroleum feed stocks. Thus, all of the lower alkene monomers with which the present invention is concerned are available as articles of commerce.

The lower alkene polymer typically has a molecular weight between about 250, preferably about 300, and about 500, preferably about 325 to about 475, more preferably from about 350 to about 450, and most preferably from about 380 to about 420. The lower alkene polymer, as later discussed, is conveniently utilized for the alkylation of benzene or other aromatic compounds which are then further converted to form alkylated aromatic sulfonic acids which are utilized as detergent substrates for overbasing in the lubricant industry. Other uses, as later described herein, are the alkylation of acylating agents such as carboxylic acids and anhydrides, phenols and the like.

The catalyst system employed herein has as a first component boron trifluoride. The boron trifluoride may be obtained as the gas commercially, generated in situ or obtained as the etherate.

The second component utilized as part of the catalytic system is a strong acid such as a mineral acid. The mineral acids include the hydrogen halides, sulfuric acid, sulfurous acid and the various phosphoric acids. Among the phosphoric acids are $H_3PO_4$, $HPO_3$ and $H_4P_2O_7$. Any strong acid may be employed provided that the desired polymer is obtained. Thus, while phosphoric acid or sulfuric acid are the preferred acids for use herein, any highly protic acid may be used. Thus, strong acid resins such as Amberlyst ™ may be used. The amount of acid is that amount sufficient to catalyze the reaction typically about 0.005% to about 1% by weight of the polymer.

It is also possible to superacidify the acids employed herein. Thus, it is possible to use oleum (fuming sulfuric acid) or glacial phosphoric acid through the introduction of $P_2O_5$ to phosphoric acid in order to increase the acid strength. It has been found, however, that the typical commercial strength acid, e.g., 85% phosphoric or 98% sulfuric are adequate within the present invention to accomplish the desired polymerization of the lower alkene monomer to the lower alkene polymer. Typically, a preferred acid is an aqueous solution containing 70-95% by weight of phosphoric acid ($H_3PO_4$).

The boron trifluoride is employed such that it saturates the reaction mixture. Due to the strength of both the acid and the corrosive nature of the source of boron trifluoride, it is suggested that the reactions be run in a glass lined or stainless steel vessel. Under the conditions with which the present invention is practiced, it is acceptable to run at atmospheric pressure.

The catalyst system as previously discussed may be immobilized, heterogeneous, supported or in any other manner in which catalysts are utilized provided that the objects of the invention are met. The substrates which may be employed in the present invention include kieselguhr, clay, charcoal, aluminosilicates, alumina, silica, diatomaceous earth and various other metal silicates.

A heterogeneous catalyst system would, for example, simply be a mixture of $BF_3$ (boron trifluoride) and the acid, e.g., phosphoric. Typically, the heterogeneous system is obtained by bubbling gaseous boron trifluoride through the liquid acid/monomer/polymer mixture.

It is believed that the restrictive temperature conditions under which the lower alkene monomer is polymerized in the presence of the catalyst system gives the high degree of unsaturation content retained in the polymer together with the narrow molecular weight distribution. In the present invention, it is highly desired that the product be mono-unsaturated so that it may be alkylated onto an aromatic ring in the desired manner. The subsequent alkylation conditions are such that internal unsaturation in a polymer of similar molecular weight but prepared outside the scope of the present invention will result in degradation of the polymer or products other than the desired alkylation products.

The temperature conditions under which the desired alkylating agents are obtained are from about $-3°$ C. to about $-30°$ C., preferably about $-5°$ C. to about $-25°$ C. and most preferably about $-8°$ C. to about $-20°$ C.

The following are examples of alkylating agents suitable for detergents.

EXAMPLE A

A mixture is prepared comprising 200 grams hexane, 8 grams of phosphoric acid and 80 grams of DD1600 filter aid. The filter aid is utilized as the catalyst substrate. The premixture is obtained by first combining the filter aid and the hexane and thereafter adding 85% phosphoric acid to the mixture. The mixture is stirred for about 30 seconds.

A 12-liter, 10-necked round bottom flask equipped with a stirrer, thermometer, dry ice/isopropanol condenser, 4 surface inlet tubes for propylene and 1 surface inlet tube for boron trifluoride is charged with the material described above. An additional 2200 grams of hexane solvent is added to the system.

The mixture described above is cooled to $-20°$ C. and boron trifluoride is introduced to the system at 1.0 cubic foot per hour (1.25 moles/hour) for 20 minutes until the system is saturated. Evidence of saturation will be observed by boron trifluoride fumes venting from the condenser. The rate of flow of the boron trifluoride is then adjusted to about 0.2 cubic foot per hour (0.25 mole/hour). The latter rate of boron trifluoride flow is maintained for the duration of the polymerization reaction.

Propylene gas is then added through the remaining 4 inlet tubes at 20 cubic feet per hour total (25 moles/hour). The temperature bath is maintained at $-46°$ C. to $-60°$ C. to hold the $-20°$ C. charge temperature. The flow rate of propylene is about 1 drop per minute condensed on a dry ice condenser during the propylene addition. A total of 121 cubic feet (150 moles) of propylene total is charged to the reaction vessel.

The propylene and boron trifluoride feed are stopped and the charge is neutralized with 80 grams of caustic soda liquid (50% aqueous). The charge is stirred for several hours to ensure neutralization. The product (lower alkene polymer) is filtered through a cake of approximately 30 grams of the DD1600 filter aid.

The product is then vacuum stripped in a separate 12-liter, 3-necked flask at 30 mm Hg (4 KPa) at 100° C. to remove the hexane. A second strip at 9 mm Hg (1.2 KPa) at 163° C. to remove the light ends results in the desired product in the amount of 5,418 grams.

The process will give near quantitative conversion to the polymer when a closed system is employed, e.g., the excess propylene is not vented.

EXAMPLE B

A 12-liter, 10-necked round bottom flask is equipped with a stirrer, thermometer, dry ice/isopropanol condenser, 4-surface inlet tubes for propylene and 1-surface inlet tube for boron trifluoride. The reaction vessel is immersed in a cooling bath and is charged with 2400 grams of hexane, 120 grams of silica gel and 12 grams of phosphoric acid in that order. The foregoing mixture is stirred at high speed for 15 minutes.

The reaction mixture is cooled to $-27°$ C. and boron trifluoride is added to the system at 1.5 cubic feet per hour (2.25 moles/hour) for a period of 23 minutes until the system is saturated. The boron trifluoride flow rate is then changed to 0.1 to 0.2 cubic feet per hour for the duration of the polymerization. The foregoing flow rate is sufficient to maintain saturation within the system.

Propylene is added through the remaining inlet tubes. The initial feed rate is 20 cubic feet per hour (30 moles/hour). In order to maintain the reaction mixture at $-20°$ C., the flow rate of propylene is decreased by 20%. The bath temperature is maintained at $-48°$ C. to $-50°$ C. to maintain the $-20°$ reaction temperature. The reaction is conducted over a period of about 5½ hours at a rate of 1 drop of propylene per minute condensed on the dry ice condenser during the propylene addition. A total 98.3 cubic feet (148 moles) of propylene was charged to the reactor during the reaction time.

Following complete addition of the propylene, the boron trifluoride feed is stopped and the reaction mixture is neutralized with 200 grams of calcium hydroxide. The reaction mixture is stirred for several hours to ensure neutralization and the charge is filtered through 50 grams of DD1600.

The filtered reaction mixture is then placed in another reaction vessel and vacuum stripped at 100° C and 72mm mercury (9.5 Kpa) to remove the hexane. Subsequently, the reaction mixture is raised to 161° C. and a vacuum of 24 mm mercury (3.2 KPa) issued to remove 7 grams of light end material leaving a residue of 4,386 grams of the liquid product.

A detergent alkylate of benzene, toluene or xylene is basically made by reacting the aromatic component with the polymer of Example A or B.

The next component to be discussed in the present invention is the unsaturated hydrocarbon component. Generally, the unsaturated hydrocarbon component has the same description as given previously for the alkylating agent.

The unsaturated hydrocarbon herein preferably has a number average molecular weight between about 600 and 3,000. Preferably, the unsaturated hydrocarbon has a number average molecular weight of about 650 to about 2,500, and yet more preferably about 700 to about 2,000. The abbreviation Mw is the conventional symbol representing weight average molecular weight, and Mn is the conventional symbol representing number average molecular weight. Gel permeation chromatography (GPC) is a method which provides both weight average and number average molecular weights as well as the entire molecular weight distribution of the polymers. For purpose of this invention a series of fractionated polymers of isobutene, polyisobutene, is used as the calibration standard in the GPC.

The techniques for determining Mn and Mw values of polymers are well known and are described in numerous books and articles. For example, methods for the determination of Mn and molecular weight distribution of polymers is described in W. W. Yan, J. J. Kirkland and D. D. Bly, "Modern Size Exclusion Liquid Chromatographs,", J. Wiley & sons, Inc., 1979.

The unsaturated hydrocarbon utilized herein may be the polypropylene as previously described, or it may be a material such as obtained from polybutene and in particular a polyisobutylene. The desired unsaturated hydrocarbons are alpha-olefins or vinylidenes.

An additional feature of the present invention is the use of a second lower molecular weight unsaturated hydrocarbon. Typically, the lower molecular weight unsaturated hydrocarbon will have a number average molecular weight of about 200 to about 599. More preferably the second unsaturated hydrocarbon will have a molecular weight of about 225 to about 550 and most preferably from 250 to 475.

PROCESSING

The organic sulfonic acid and the unsaturated hydrocarbon may be combined in any particular fashion which is effective for obtaining the objectives in the present invention. Typically, the organic sulfonic acid is first obtained by sulfonating the alkylated aromatic compound through any conventional method. Among the methods which may be employed for sulfonation to obtain the organic sulfonic acid are oleum (fuming sulfuric acid), chloro sulfonic acid, or direct sulfur trioxide sulfonation.

There are numerous types of equipment available for the preparation of the organic sulfonic acid. In the present case is it preferred to utilize a falling film reactor.

The sulfonation reaction is often completed with an appreciable amount of sulfur dioxide present in the reaction mixture. The sulfur dioxide may be present as a by-product generated during sulfonation, and as well, as a diluent or contaminant in the original sulfur trioxide source.

It is desirable to remove the sulfur dioxide present in the reaction mixture containing the organic sulfonic acid prior to or substantially contemporaneous with the introduction of the unsaturated hydrocarbon. The method of reducing the sulfur dioxide content of the reaction mixture is typically by blowing with a relatively inert gas. The inert gases which may be utilized in the present invention are any gas which does not materially effect the outcome of the invention with regard to obtaining the stated objectives herein. The gases which are typically employed include nitrogen, carbon dioxide and air. The gases are preferably dry, however, some moisture may be tolerated in the gas. A particularly convenient method for removing the sulfur dioxide is to blow the gas through the reaction mixture with a cocurrent stream of the unsaturated hydrocarbon introduced at the same time.

The temperatures at which the unsaturated hydrocarbon are combined with the organic sulfonic acid are typically at about 70° F. (23° C.) to about 175° F. (80° C.); more preferably 80° F (27° C.) to about 165° F. (74° C.).

The mixture of the organic sulfonic acid and the unsaturated hydrocarbon is typically raised to a temperature of about 140° F. (60° C.) to about 350° F. (177° C.) after the mixture is formed. Preferably, the mixture of the organic sulfonic acid and the unsaturated hydrocarbon are heated to a temperature of 180° F. (82° C.) to about 300° F. (149° C.) after the mixture is formed.

The amount of the unsaturated hydrocarbon employed with the organic sulfonic acid is typically at a weight ratio of the organic sulfonic acid to the unsaturated hydrocarbon of about 10:1 to about 1,000:1, preferably about 20:1 to about 250:1.

The amount of the unsaturated hydrocarbon of the present invention which is employed may be reduced as described below. The unsaturated hydrocarbon may be lessened by including the lower molecular weight unsaturated hydrocarbon as previously discussed. The higher molecular weight unsaturated hydrocarbon may be used in a weight ratio to the lower molecular weight unsaturated hydrocarbon at levels of about 5:1 to about 1:5, preferably about 3:1 to about 1:3.

When using the lower molecular weight unsaturated hydrocarbon the positive effect of utilizing the unsaturated hydrocarbon as a diluent oil for the detergent composition is reduced. That is, the organic sulfonic acids of the present invention are typically converted to salts and overbased for use as motor oil detergent additives. The additives require substantial amounts of highly refined oil to prepare concentrates of the additives which are ultimately diluted in the preparation of the motor oil. Thus the unsaturated hydrocarbon has a secondary effect in the present invention in being useful to reduce the amount of diluent oil utilized in the composition.

It is desirable in the present invention to conduct the operation described herein such that the organic sulfonic acid has the color improved following treatment as described herein when compared to a an alkyl substituted sulfonic acid which is not treated with the unsaturated hydrocarbon. The improvement in color is typically observed as a black acid treated according to the present inventions, and converted to the neutral calcium salt of the sulfonic acid, becomes mahogany in color. The color improvement may be determined by ASTM test D1500-87.

It is also observed that the present invention stabilizes the organic sulfonic acid to elevated temperatures. That is, heat treatment of the organic sulfonic acid may occur following the treatment with the unsaturated hydrocarbon. The treatment to remove sulfur dioxide concurrently, or prior to the sulfur dioxide removal further improves the color of the composition.

It will also be observed in the present invention that the amount of filter cake may be reduced as well as the amount of inactives in the overall composition. The filter cake is the resultant material obtained after a filter aid is used to remove the inactives. The typical filter aids utilized in the present invention are diatomaceous earths.

The inactives are materials which are apparently obtained from the sulfur dioxide present and which provide no valuable benefit to the overall composition. Thus the removal of the inactives which include sulfuric acid provides a greater active content of the product as well as better color.

FURTHER PROCESSING AND ADDITIONAL INGREDIENTS

Typically the organic sulfonic acids of the present invention are converted to various alkali metal or alkaline earth metal salts which are then overbased. The alkali metal salts which are typically most useful are lithium and sodium. The alkaline earth metal salts which are often obtained are calcium, magnesium or barium salts. Typical overbased detergent products are described in U.S. Pat. No. 4,941,984 to Chamberlin III and Zalar issued Jul. 17, 1990.

Additional components which may be utilized in the present invention include typical motor oil components. Thus oils of lubricating viscosity may be utilized in the present invention as a base for the eventual use of the organic sulfonic acid. Additional components which may be utilized herein are various zinc salts as extreme pressure agents in a composition such zinc dithiodialkyl phosphates, hydrocarbon soluble ashless dispersants of the type described in U.S. Pat. 4,234,435, various metal containing antioxidants such as certain oil soluble copper salts, various non-metallic antioxidants, and viscosity improvers such as high molecular weight polymers. The compositions of the present invention may contain other components such as dyes, pour point depressants and the like.

What follows hereafter is an example of the present invention.

EXAMPLE I

An alkylbenzene sulfonic acid is obtained wherein the alkylating agent used to make the acid contains an average of 22 carbon atoms and is derived from polypropylene. The acid is removed from the sulfonation unit and is maintained at a temperature of 150° F. (66° C.). To the sulfonic acid is introduced two parts of an olefin having a number average molecular weight of 900 per 100 parts of the acid. The addition is facilitated by stirring the entire reaction mixture.

Air is blown through the bottom of the reactor to facilitate removal of sulfur dioxide.

While the air is being blown into the reaction mixture the temperature of the reaction mixture is controlled to 200° F. (93° C.). The reaction mixture is held at the 200° F temperature for a period of about eight hours.

Thereafter the reaction mixture may be further processed to form a calcium salt of the alkylbenzene sulfonic acid. The calcium salt may then be subsequently overbased and utilized as a detergent for an automobile motor oil.

What is claimed is:

1. In the process of treating an organic sulfonic acid the steps comprising; contacting the organic sulfonic acid with at least 0.3 weight part of an unsaturated hydrocarbon per 100 weight parts of the organic sulfonic acid to obtain a mixture, wherein the unsaturated hydrocarbon has a number average molecular weight between about 600 and 3,000 wherein the organic sulfonic acid is neutralized and contacted with a filter aid.

2. The process of claim 1 wherein the mixture of the sulfonic acid and the unsaturated hydrocarbon are at about 70° F. (23° C.) to about 175° F. (80° C.) immediately after forming the mixture.

3. The process of claim 1 wherein the mixture of the organic sulfonic acid and the unsaturated hydrocarbon are heated to a temperature of about 140° F. (60° C.) to about 350° F. (177° C.) after the mixture is formed.

4. The process of claim 1 wherein the organic sulfonic acid is contacted with a non-reactive gas.

5. The process of claim 3 wherein the amount of unsaturated hydrocarbon added to the organic sulfonic acid is sufficient to improve the color of the resultant mixture when compared to an organic sulfonic acid which is not treated with the unsaturated hydrocarbon.

6. The process of claim 1 wherein the organic sulfonic acid further contains a second unsaturated hydrocarbon having a number average molecular weight of about 200 to about 599.

7. The process of claim 1 wherein the organic sulfonic acid is an alkyl substituted aromatic sulfonic acid.

8. The process of claim 4 wherein the contacting of the organic sulfonic acid with the non-reactive gas lowers the level of any sulfur dioxide present.

9. The process of claim 8 wherein the treatment of the organic sulfonic acid with the non-reactive gas to lower the presence of sulfur dioxide is done prior to, or substantially contemporaneously with, the introduction of the unsaturated hydrocarbon.

10. The process of claim 1 wherein the unsaturated hydrocarbon is an alpha olefin.

11. The process of claim 3 wherein the mixture of the organic sulfonic acid and the unsaturated hydrocarbon are heated to a temperature of about 180° F. (82° C.) to about 300° F. (149° C.) after the mixture is formed.

12. The process of claim 11 wherein the organic sulfonic acid is an alkyl substituted aromatic sulfonic acid.

13. The process of claim 2 wherein the mixture of the organic sulfonic acid and the unsaturated hydrocarbon are at about 80° F. (27° C.) to about 165° F. (74° C.) immediately after forming the mixture.

14. The process of claim 12 wherein the alkyl substituted aromatic sulfonic acid is an alkyl substituted toluene sulfonic acid.

15. The process of claim 4 wherein the non-reactive gas is selected from the group consisting of nitrogen, air and carbon dioxide and mixtures thereof.

16. The process of claim 12 wherein the alkyl substituted aromatic sulfonic acid is an alkyl substituted xylene sulfonic acid.

17. The process of claim 12 wherein the alkyl substituted aromatic sulfonic acid is an alkyl substituted benzene sulfonic acid.

18. The process of claim 12 wherein the mixture of the organic sulfonic acid and the unsaturated hydrocarbon are heated to a temperature of about 140° F. (60° C.) to about 300° F. (149° C.) after the mixture is formed.

19. The process of claim 1 wherein the unsaturated hydrocarbon is selected from the group consisting of polypropylene and a polybutene and mixtures thereof.

20. The process of claim 19 wherein the unsaturated hydrocarbon is polyisobutylene.

21. The process of treating a mixture of an alkyl substituted aromatic sulfonic acid and a source of sulfur dioxide wherein an alkyl substituted aromatic compound is contacted with a sulfonating agent to obtain the alkyl substituted aromatic sulfonic acid, and the alkyl substituted aromatic sulfonic acid and source of sulfur dioxide is then processed to reduce the sulfur dioxide content of the mixture by introducing a relatively non-reactive gas to the mixture and maintaining the mixture at a temperature of about 70° F. (23° C.) to about 175° F. (80° C.) for a period of time sufficient to reduce the sulfur dioxide content, and contacting the alkyl substituted aromatic sulfonic acid with an unsaturated hydrocarbon having a number average molecular weight between about 600 and 3,000 wherein the alkyl substituted aromatic sulfonic acid is neutralized and contacted with a filter aid.

22. The process of claim 21 wherein the mixture following contacting with the unsaturated hydrocarbon is heated to a temperature of from 140° F. (60° C.) to 350° F. (177° C.).

23. The process of claim 21 wherein the alkyl substituted aromatic sulfonic acid is contacted with a second unsaturated hydrocarbon having a number average molecular weight of about 200 to about 599.

24. The process of claim 22 wherein the amount of unsaturated hydrocarbon added to the alkyl substituted aromatic sulfonic acid is sufficient to improve the color of the resultant mixture when compared to an alkyl substituted sulfonic acid which is not treated with the unsaturated hydrocarbon.

25. The process of claim 21 wherein sulfur dioxide is generated during the formation of the alkyl substituted aromatic sulfonic acid.

26. The process of claim 21 wherein the treatment of the alkyl substituted aromatic sulfonic acid with the non-reactive gas to reduce the presence of sulfur dioxide is done prior to, or substantially contemporaneously with, the introduction of the unsaturated hydrocarbon.

27. The process of claim 21 wherein the unsaturated hydrocarbon is an alpha olefin.

28. The process of claim 21 wherein the mixture of the alkyl substituted aromatic sulfonic acid and the unsaturated hydrocarbon are heated to a temperature of about 180° F. (82° C.) about 399° F. (149° C.) after the mixture is formed.

29. The process of claim 21 wherein the unsaturated hydrocarbon is selected from the group consisting of polypropylene and a polybutene and mixtures thereof.

30. The process of claim 29 wherein the unsaturated hydrocarbon is polyisobutylene.

31. The process of claim 21 wherein the mixture of the alkyl substituted aromatic sulfonic acid and the unsaturated hydrocarbon are at about 80° F. (27° C.) to about 165° F. (74° C.) immediately after forming the mixture.

32. The process of claim 21 wherein the alkyl substituted aromatic sulfonic acid is an alkyl substituted toluene sulfonic acid.

33. The process of claim 21 wherein the alkyl substituted aromatic sulfonic acid is an alkyl substituted benzene sulfonic acid.

34. The process of claim 21 wherein the alkyl substituted aromatic sulfonic acid is an alkyl substituted xylene sulfonic acid.

35. The process of claim 21 wherein the non-reactive gas is selected from the group consisting of nitrogen, air and carbon dioxide and mixtures thereof.

* * * * *